United States Patent [19]
Suh et al.

[11] Patent Number: 5,859,016
[45] Date of Patent: Jan. 12, 1999

[54] MEMORY ENHANCING AND ANTI-DEMENTIA AGENT CONTAINING DEHYDROEVODIAMINE HC1 AS ACTIVE INGREDIENT

[75] Inventors: Yoo-Hun Suh; Sam-Sik Kang; Seong-Hun Kim; Cheol-Hyoung Park; Woong Choi, all of Seoul, Rep. of Korea

[73] Assignees: JE IL Pharmaceutical Co., Ltd.; Yoo-Hun Suh, both of Seoul, Rep. of Korea

[21] Appl. No.: 815,678

[22] Filed: Mar. 12, 1997

Related U.S. Application Data

[63] Continuation of Ser. No. 666,852, Jun. 19, 1996, abandoned.

[30] Foreign Application Priority Data

Jun. 20, 1995 [KR] Rep. of Korea .................. 1995 16426

[51] Int. Cl.$^6$ ................................. A61K 31/505
[52] U.S. Cl. ............................... 514/257
[58] Field of Search ........................... 514/257

[56] References Cited

PUBLICATIONS

S. Loh et al., "Ionic Mechanisms Responsible for the Anti-arrhythmic Action of Dehydroevodiamine in Guinea–pig Isolated Cardiomycites", Br. J. Pharmacol., 106:517–523 (1992).

C.B. Millard et al., "Anticholinesterases: Medical Applications of Neurochemical Principles", J. Neurochem., 64(5):1909–1918 (1995).

Y. Kanaoka et al., "Polyphosphate Ester as a Synthetic Agent", Chem. Pharm. Bull. 15(1):101–107 (1967).

A. Haji et al., "Increased Feline Cerebral Blood Flow Induced By Dehydroevodiamine Hydrochloride From Evodia Ruttaecarpa[1]", J. Nat. Prod., 57(3):387–389 (1994).

M. Yang et al., "The Hypotensive and Negative Chronotropic Effects of Dehydroevodiamine", Euro. J. Pharm., 182:537–542 (1990).

H. Yang et al., "Hypotensive Effects of Dehyroevodiamine, A Quinazolino–carboline Alkaloid Isolated From Evodiae Rutaecarpa Rutaecarpa", Asia Pacific Journal of Pharmacology, 3:191–196 (1988).

N. Whittaker et al., "The Synthesis of Emetine and Related Compounds", J. Chem. Soc. pp. 85–89 (1969).

*Primary Examiner*—Phyllis G. Spivack
*Attorney, Agent, or Firm*—Finnegan, Henderson, Farabow, Garrett & Dunner L.L.P.

[57] ABSTRACT

Dehydroevodiamine-HCl, a constituent of *Evodia rutaecarpa* Benth. (DHED) exhibits anti-AChE activity and improves the memory impairment of animals produced by scopolamine in the passive avoidance test. Thus, DHED can be a potent, long term memory enhancing and anti-dementia agent if it is used together with a pharmaceutically acceptable carrier.

23 Claims, 6 Drawing Sheets

MEMORY ENHANCING AND ANTI-DEMENTIA AGENT CONTAINING DEHYDROEVODIAMINE HC1 AS ACTIVE INGREDIENT

CROSS REFERENCE TO RELATED APPLICATION

This application is a continuation of U.S. patent application Ser. No. 08/666,852, filed Jun. 19, 1996, now abandoned.

FIELD OF THE INVENTION

This invention relates to a memory enhancing and anti-dementia agent containing dehydroevodiamine-HCl as an active ingredient, expressed by the following formula (I), and more particularly, to use, as an anti-dementia agent, of a pharmaceutical containing dehydroevodiamine-HCl, for inhibiting acetylcholinesterase activity and enhancing the memory.

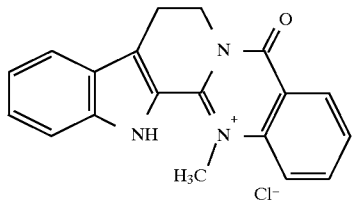

BACKGROUND OF THE INVENTION

Senile dementia, also known as Alzheimer's disease, affects a number of people around the world in spite of races, sex, etc. In view of the current situation that the aging population is on the sharp increase, senile dementia poses one of the serious health problems in the 21st century. Presently, there are presumably more than 300,000 patients suffering from senile and vascular dementia in Korea.

In the case of western countries, Alzheimer's disease is known to be present in about 10 percent of those over 65 years old and in about 40 to 50 percent of those over 80 years old. In addition, the number of patients suffering from Alzheimer's disease has been growing over time in Japan and China.

Although a number of theories recently have been proposed concerning the cause of Alzheimer's disease, such as viral infections, toxic poisoning by aluminum and amyloid beta-protein deposited on neuronal cells, the cause of this disease is not obvious.

Therefore, causative therapy cannot be applied due to the unknown pathogenesis of Alzheimer's disease. However, since the most noticeable characteristics in dementia patients are the reduction of chlolinergic functions in the central nervous system, many researchers have tried to improve the symptoms of Alzheimer's disease, through the enhancement of the level of acetylcholine in the brain by administering an acethylcholine precursor, cholinergic agonist or acetylcholinesterase inhibitor (hereinafter called "AChEI").

As a result of intensive endeavors in research, some drugs, such as SDZ ENA 71 (carbamates and a series of miotone derivatives) or L-Huperzine A, were developed, but they have yet to exhibit satisfactory anti-dementia effects. Furthermore, the development of AChEI specific to the CNS is still in the infant stage.

The currently available anti-dementia agents around the world include the following: i) AChEI drugs for improving the symptoms of cognitive deficits through the elevation of acetylcholine level, ii) metabolic drugs increasing the energy metabolism of neurons nonspecifically, and iii) blood-circulation enhancer improving the circulation of micro-blood. However, the effects of these drugs are temporal and marginal, and there is no report that these drugs were useful as a remedy for Alzheimer's disease patients. Further, the side-effects of conventional drugs, due to the stimulation of parasympathetic nerve cells, include nausea, vomiting and bronchoconstriction. Other side-effects, such as depression, insomnia, hypertension, and constipation, have been reported.

Therefore, there is an urgent need to develop an anti-dementia agent displaying a remarkable therapeutic efficacy for dementia, while improving cerebral pathological change with less adverse effects.

SUMMARY OF THE INVENTION

To overcome the aforementioned disadvantages associated with the conventional drugs, the inventors have endeavored to find a novel candidate substance as an anti-dementia agent from natural products. As a result, it was found that dehydroevodiamine-HCl (hereinafter called "DHED"), separated from *Evodia rutaecarpa* Benth. and expressed by the formula (I), had a novel acetylcholinesterase (hereinafter called "AChE") activity, and could reverse the amnesic effect of scopolamine in a passive avoidance test. Thus, this invention has been completed.

DETAILED DESCRIPTION OF THE INVENTION

Therefore, the object of this invention is to provide an anti-dementia agent containing DHED as an active ingredient, which inhibits AChE activity.

This invention is described in more detail below.

This invention is characterized by an anti-dementia agent containing dehydroevodiamine-HCl and its functional analogues as active ingredients, together with a pharmaceutically acceptable carrier.

DHED, an active ingredient for the treatment of dementia according to this invention, is obtained from a natural extract separated from *Evodia rutaecarpa* Benth. or from chemical synthesis.

*Evodia rutaecarpa* Benth. has potent antibacterial and insecticidal activities in vitro against some kinds of Vibrio cholerae, dermatophyte and parasites, such as Ascaris, etc. It also has been reported to be effective in uterine contraction, hypertension and hyperthermia, as well as in the treatment of eczema or neurodermatitis.

DHED, extracted from *Evodia rutaecarpa* Benth. and expressed by the formula (I), has been reported to have various biological effects, such as hypertensive [Yang H. Y. et al., Asian Pac. J. Pharmacol. 3, 191~196 (1988)], negative chronotrophic [Yang M. C. et al., Eur. J. Pharmacol., 182, 537~542 (1990)], ion channel depressant [Loh S. H. et al., Br. J. Pharmacol., 106, 517~523 (1992)] and cerebral blood flow enhancing [Haji A. et al., J. Nat. Prod., 57, 387~389 (1994)] activities.

Further, there are many clinical reports in which AChEI is used as an effective therapeutic agent for the treatment of glaucoma, myasthenia gravis and paralytic ileus [Millard C. B. et al., J. Neurochem., 64, 1909~1918 (1995)].

In order to separate DHED from *Evodia rutaecarpa* Benth., *Evodia rutaecarpa* Benth. was extracted with 80% methanol. This procedure was repeated twice, and the methanol solution was concentrated under vacuum. $CH_2Cl_2$ fractions obtained from the methanol extracts were chromatographed on a silica gel column, and this resulted in subfractions. Then, AChE inhibitory activities on each subfraction were determined, and the one subfraction showing the most potent inhibition of AChE activity was selected.

To find a component exerting an inhibitory effect on AChE activity from the subfraction, it was further purified with methanol to give a crystal compound having a single component. To identify the structure of this crystal, its m.p., UV, IR, MS and NMR were measured, together with various physiochemical properties.

From the spectral data, this component, present in the subfraction and inhibiting the AChE, was identified as a DHED expressed by the well-known formula (I); DHED have been reported to have the effects of cerebral blood flow enhancement and hypertension.

DHED inhibited AChE activity in a dose dependent manner and non-competitive manner, confirming it is an active anticholinestrase compound in Evodia rutaecarpa.

Now that DHED, showing a strong inhibitory effect on AChE in vitro, may enhance the acetylcholine level, it is predicted that DHED may enhance memory and improve dementia.

In parallel with the analysis of such prediction, a test was designed to confirm the actual effects of DHED on memory enhancement in animals having memory deficit by a passive avoidance test. As a result, it was found that DHED was able to reverse the memory deficit of scopolamine induced amnesia.

Therefore, an anti-dementia agent of this invention contains DHED extracted from Evodia rutaecarpa Benth., together with a pharmaceutically acceptable carrier.

Further, an anti-dementia agent of this invention may also contain the synthesized form of DHED as an active ingredient instead of natural DHED extracted from Evodia rutaecarpa Benth. The process of synthesizing DHED was already reported [Chem. Pharm. Bull., 33(1), 101~107 (1967); J. Chem. Soc., 85 (1969); J.A.C.S., 29, 6186~6188 (1976); Jr. Pharm. J., Vol. 82, 619].

This invention is described in more detail by the EXAMPLES as set forth hereunder. These EXAMPLES are only intended for describing this invention. The fact that the scope of this invention is not confined to these EXAMPLES is quite evident to those of ordinary skill in this industry.

EXAMPLE 1

Preparation of Subfraction from Evodia rutaecarpa Benth.

10 kg of Evodia rutaecarpa Benth. was refluxed in a water bath with 80% methanol, and the resulting methanol solution was concentrated under reduced pressure to give a methanol extract. A mixture of $CH_2Cl_2$ and distilled water (1:1) was added to the methanol extract and then, agitated to obtain 240 g of $CH_2Cl_2$ fraction. 120 g of the $CH_2Cl_2$ fraction was chromatographed on a silica gel column (Merck 7734, USA) by gradient elution with a mixture of solvent ($CHCl_3$, $CHCl_3$:acetone=30:1(v/v), 20:1(v/v), 10:1(v/v) and $CHCl_3$:methanol=10:1(v/v), 1:1(v/v)), which resulted in subfractions. Each subfraction confirmed by thin layer chromatography (TLC) was combined with the same specific band to obtain 20 subfractions, and all these fractions were freeze-dried.

EXAMPLE 2

Determination of AChE Inhibitory Activity

In order to determine AChE inhibitory activity on each of the 20 subfractions obtained from EXAMPLE 1, 10 volumes of phosphate buffer solution (12.5 mM phosphate buffer solution at pH 7.0, including 400 mM NaCl) was added to the cerebral cortex of mice, homogenized in a Potter-Elvehjem homogenizer and centrifuged at 1,000 g for 10 min to obtain the supernatant. After adding homogenized buffer containing 0.5% triton X-100 to the supernatant, the mixtures were stirred for 30 min and centrifuged again at 10,000 for 10 min. The resulting supernatant was used as an AChE source. All extract steps were carried out at 4° C.

The freeze-dried 20 subfraction extracts of EXAMPLE 1 were initially dissolved in small amounts of distilled water and DMSO. The solution was diluted at a concentration of 200 μg/ml in phosphate buffer (100 mM sodium phosphate, pH 8.0; hereinafter called "buffer solution I"). 1.5 ml of each extract was mixed with 1.5 ml of buffer solution I, 20 μl of 75 mM acetylthiocholine iodide solution and 100 μl of buffered Ellmans reagent [10 mM DTNB (5,5-dithiobis-(2-nitrobenzoic acid)) and 17.85 mM $NaHCO_3$] and incubated at 25° C. for 10 min. Absorbance was read at 410 nm immediately after adding an enzyme to the above reaction mixtures. Reading was repeated for 5 min at 30 sec intervals in order to determine AChE inhibitory activity on each subfraction. A blank control reaction was measured by substituting saline for the enzyme.

AChE activity was calculated with the absorption coefficient 1.36 l/mmol/min. The inhibition efficacy was expressed as a percentage of enzyme activity inhibited compared with the control value (100%).

All experiments were repeated five times, and the results were analyzed by a Wilcoxon-rank sum test and Median 2-sample test.

As illustrated in FIG. 1, it was found that the No. 17 and 20 subfractions were shown to inhibit AChE activity most potently. Therefore, to find the substance inhibiting AChE activity, No. 17 subfraction among active fractions was purified with methanol several times to give a yellowish crystal compound.

EXAMPLE 3

Identification of AChE Inhibitory Substance Present in the Active Subfractions

To identify the structure of the No. 17 subfraction crystal compound obtained from EXAMPLE 2, its m.p., UV, IR, MS and NMR (attached as FIG. 2) were measured to find its physiochemical and spectral properties.

m.p.: 249°–251° C.

UV $\lambda_{max}$(MeOH)nm(log l: 246(4.08),305(sh,3.64),314 (3.71),365(4.36)

IR $\nu_{max}$(KBr)cm$^{-1}$:3437, 3235, 1709, 1611, 1557, 1501, 1350, 1339, 1285, 1219, 1103, 766, 721, 687

MS m/z(rel. int):302[M-Cl]$^+$ $^1$H-NMR(300 MHz, DMSO-d$_6$) δ: 3.35(2H, t, J=6,9Hz, H-6), 4.47(2H, t,J=6.7Hz, H-5), 4.37(3H, s, $CH_3$), 7.29(1H, brt, J=7.6Hz, H-10), 7.54(1H, brt, J=7.6Hz, H-11), 7.69(1H, brd, J=8.6Hz, H-12), 7.81(1H, dt, J=1.2, 8.5Hz, H-18), 7.89(1H, brt, J=8.2Hz, H-9), 8.14(1H, dt, J=1.1, 8.6Hz, H-17), 8.20(1H, brd, J=8.3Hz, H-16), 8.36(1H, brd, J=7.8Hz, H-19), 12.33(1H, s, NH)

$^{13}$C-NMR(75.5 MHz, DMSO-d$_6$) δ: 18.44(C-6), 40.64 ($CH_3$), 42.02(C-5), 113.37(C-12), 118.44(C-16), 118.65(C-20), 120.05(C-2), 121.50(C-10), 121.56(C-9), 123.26(C-8), 127.60(C-9), 128.55(C-18), 128.75(C-11), 130.38(C-7), 136.57(C-17), 139.62(C-15), 141.30(C-13), 149.94(C-3), 158.09(C=0)

These results indicate that DHED, an already known substance, is the active component in the No. 17 subfraction to inhibit AChE activity.

EXAMPLE 4

Synthesis of DHED

DHED, a proven AChE inhibitor from the EXAMPLE, can be synthesized in the following process. Its measurement results on UV, IR, MS and NMR were in agreement with those of EXAMPLE 3.

manner, and the concentration required for 50% enzyme inhibition ($IC_{50}$) was 37.8 $\mu$M. Further, FIG. 4 shows Lineweaver-Burke plots of AChE activity over a range of substrate concentrations (23 to 230 $\mu$M) in the presence (a) and absence (b) of DHED (40 $\mu$M). It was confirmed that DHED inhibited AChE activity in a non-competitive manner. Because the facts demonstrate that DHED, showing a strong inhibitory effect on AChE in vitro, increases the acetylcholine level, it is predicted that DHED can improve memory deficits.

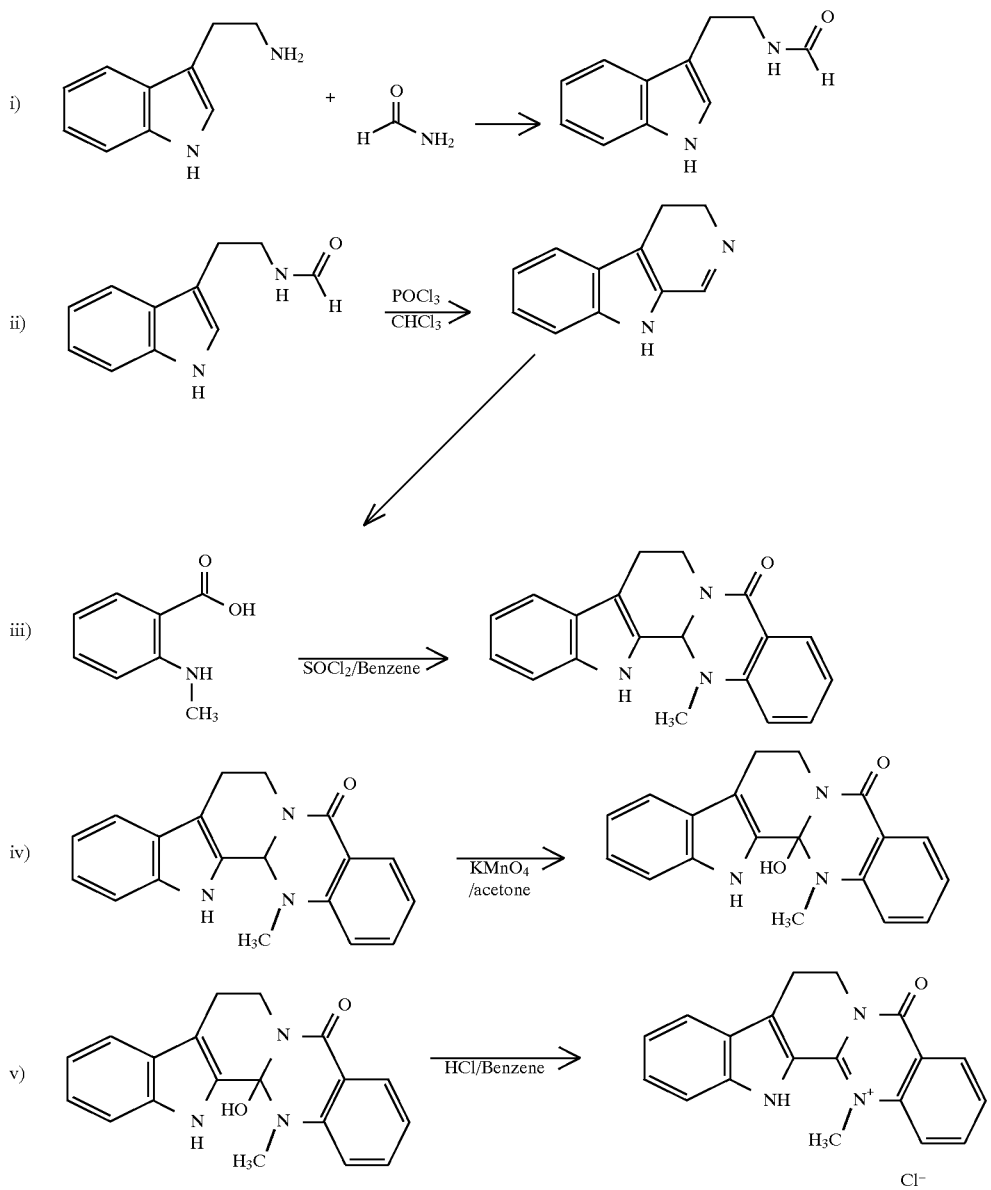

EXAMPLE 5

Inhibition of AChE Activity by DHED

FIG. 3 shows the dose-dependent inhibition of AChE activity by DHED obtained from EXAMPLE 3 or EXAMPLE 4. It was found from FIG. 3 that DHED showed a strong inhibitory effect on AChE in a dose-dependent

EXAMPLE 6

Determination of Anti-amnesic Activity by DHED

To investigate the memory enhancement of DHED in vivo, a single and repeated administration of DHED were given to rats in a passive avoidance test.

Measurement of memory enhancement by a single administration of DHED

Male Sprague-Dawley rates weighing 200~250 g (12~16 weeks) which had been maintained on a 12 h/12 h light-dark cycle were used for a passive avoidance test. Food and water were available ad libitum. An automated system with a shuttle box (Model PACS-30, Columbus Instruments International Company) was used to evaluate the effects of the extracts on learning and memory essentially as described (11). The shuttle box was divided into two chambers of equal size (19"L×9"W×10.875"H). These compartments were separated by a guillotine door (3" L×2.625" W). A light chamber is equipped with an illuminator. Rats can go to the dark chamber through a guillotine door. Each rat was initially placed in the light chamber, and the door was opened. The rats displayed an explorative behavior for a while and entered the dark compartment. When the rats entered the dark compartment, the door was automatically closed. Training was repeated until the rat entered the dark compartment within 20 sec (training trial).

At 24 hours after the training trial, scopolamine (1 mg/kg) or the same volume of saline was intraperitoneally injected to the rats. After 30 min, DHED (6.25 mg/kg) or tacrine (6.25 mg/kg) was given to the rat intraperitoneally. After another 30 min, the rat was placed in the illuminated chamber. When the rat entered the dark chamber, the guillotine door was automatically closed and electrical foot shock (1 mA) was delivered for 3 sec through the grid floor (acquisition trial). At 24 hours after the acquisition trial, the rat was again placed in the light compartment and latency to enter the dark compartment was measured for 180 sec (retention trial). If it did not enter the dark chamber within the cut-off time (180 sec), it was assigned a value of 180 sec as its latency.

FIG. 5 shows the significant memory enhancement by a single treatment with DHED in scopolamine induced amnesia.

Measurement of memory enhancement by repeated administration of DHED

To investigate the effects of repeated administration of DHED, a repeated administration of DHED was intraperitoneally given to the rats at a dose of 6.25 mg/kg. Except for the fact that DHED (6.25 mg/kg) was given to the rats once a day for 5 days before the treatment with scopolamine, the latency time was measured in the same manner as in the single administration. These results are illustrated in FIG. 6.

The results indicate that repeated pre-treatment of DHED may improve memory enhancement and more significant effects may be visible through repeated administration. It was identified that DHED can be used as an effective anti-dementia drug, if it is used together with its pharmaceutically acceptable carriers, for a long term period.

EXAMPLE 7

Safety Test

A single toxicity study of the anti-dementia agent according to this invention was measured using rats. These results showed that the $LD_{50}$ of *Evodia rutaecarpa* Benth. extracts was 705 mg/kg per body weight in subcutaneous administration and 135 mg/kg per body weight in intravenous administration [ref: Chinese Drug Encyclopedia, Shanghai Scientific & Technical Publication Co., Hwanhakkwan, 831–834 (1995)]. The lethality results by a single oral administration of DHED are as follows:

TABLE 1

No. of deaths in animals after oral administration (Unit: day)

| Sex | Dose (mg/kg) | Day after administration No. of dead animals 0 1 2 3 4 5 6 7 8 9 10 11 12 13 14 | Mortality |
|---|---|---|---|
| male | 1,000 | 0 0 0 0 0 0 0 0 0 0 0 0 0 0 0 | 0/5 |
|  | 1,500 | 0 0 0 0 0 0 0 0 0 0 0 0 0 0 0 | 0/5 |
|  | 2,000 | 0 0 0 3 1 0 0 1 0 0 0 0 0 0 0 | 5/5 |
|  | 3,000 | 0 0 1 1 0 2 0 0 0 0 0 0 0 0 0 | 4/5 |
|  | 4,000 | 0 0 1 2 1 0 1 0 0 0 0 0 0 0 0 | 5/5 |
| female | 1,000 | 0 0 0 0 0 0 0 0 0 0 0 0 0 0 1 | 1/5 |
|  | 1,500 | 0 0 0 1 1 0 0 0 0 0 0 0 0 0 0 | 2/5 |
|  | 2,000 | 0 0 0 0 0 0 0 0 0 0 0 0 0 0 0 | 0/5 |
|  | 3,000 | 0 0 1 3 1 0 0 0 0 0 0 0 0 0 0 | 5/5 |
|  | 4,000 | 0 0 0 0 1 2 0 0 1 1 0 0 0 0 0 | 5/5 |

These results indicate that the $LD_{50}$ of a DHE-containing pharmaceutical composition according to this invention is 2,000 mg/kg per body weight after a single administration. Therefore, DHED of this invention, an inhibitor of AChE activity contained in *Evodia rutaecarpa* Benth., may be safely used in the effective range of oral and peripheral administration as in the following.

EXAMPLE 8

Dosage Regimen and Therapeutic Dose

In the case of an adult (body weight: 50 kg), a dose of 10 mg to 250 mg should be orally administered. When DHED is peripherally used, a dose of 10 mg to 150 mg should be intravenously administered, while a dose of 10 mg to 200 mg may be injected subcutaneously or intramuscularly.

According to this invention, the pharmaceutical composition containing DHED as an active ingredient, which inhibits AChE activity, may be administered in an oral or injectable form. In addition to active ingredients, the oral dosage form, including a tablet and gelatin capsule, may include diluents (e.g., lactose, dextrose, sucrose, mannitol, sorbitol, cellulose and/or glycine) and lubricants (e.g., silica, talc, stearic acid and its magnesium or calcium salts and/or polyethylene glycol). The tablet form may also have binders (e.g., magnesium aluminum silicate, starch paste, gelatin, methylcellulose, sodium carboxymethylcellulose and/or polyvinylpyrrolidone). In some cases, it is desirable to contain disintegrants (e.g., starch, agar, alginic acid or its sodium salt or an equivalent mixture), and/or absorbents, coloring agents, flavoring agents and sweeteners. It is desirable to use isotonic aqueous solutions or suspensions as an injectable form. The injectable form may include additives, (e.g., preservatives, stabilizers, humidifiers or emulsifiers, solution enhancers, salts and/or buffering agents for controlling osmotic pressure), and it may be sterilized. Further, the injectable form may contain other different substances for treatment.

As described above in more detail, the purpose of this invention is to provide a senile and vascular anti-dementia agent containing DHED which inhibits AChE activity. It is found that DHED of this invention inhibits AChE activity and displays memory enhancement in scopolamine-induced memory impaired animals of an animal model.

Figure 1:
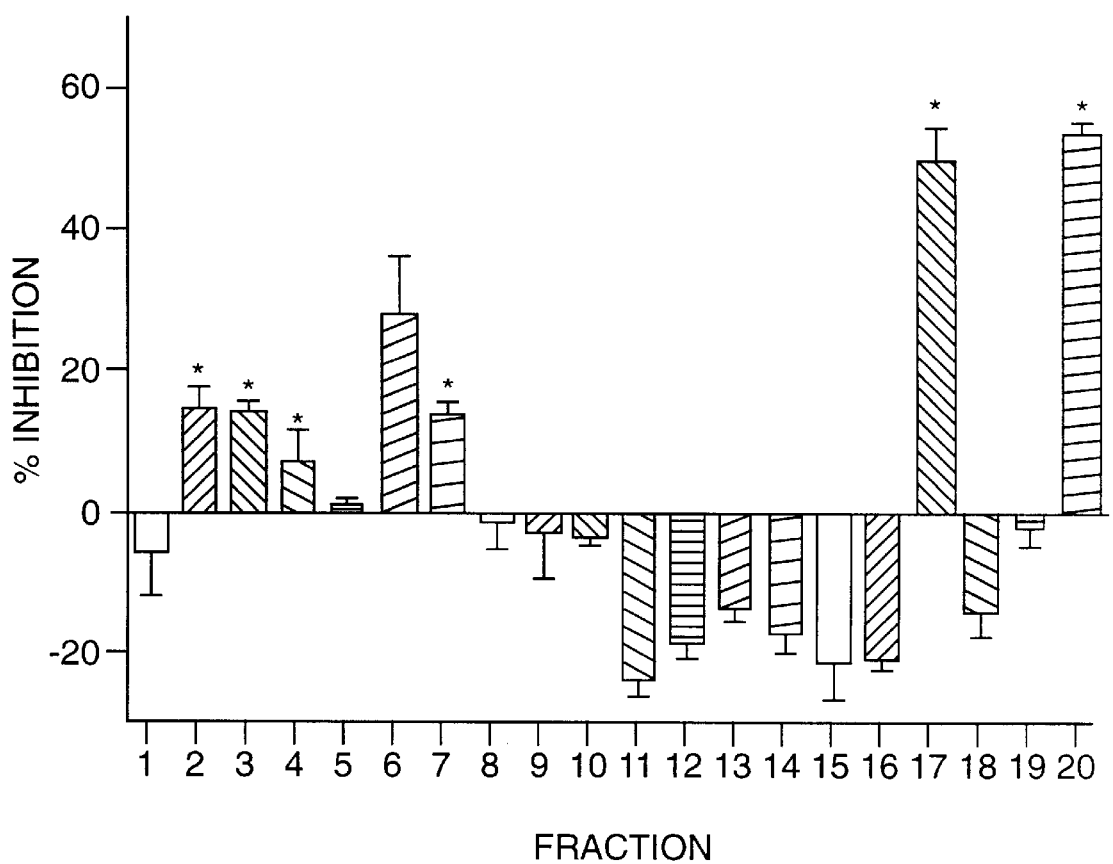
FIG. 1. Shows the effects of various subfractions (200 µg/ml) from *Evodia rutaecarpa* Bentham on acetylcholinesterase activity. The inhibition efficacy was expressed as a percentage of enzyme activity inhibited compared with the control value (100%). Each value represents mean±S. E. (n=5). * represents p<0.05 by Wilcoxon-rank sum test between the control and subfraction-treated groups.
Figure 2:
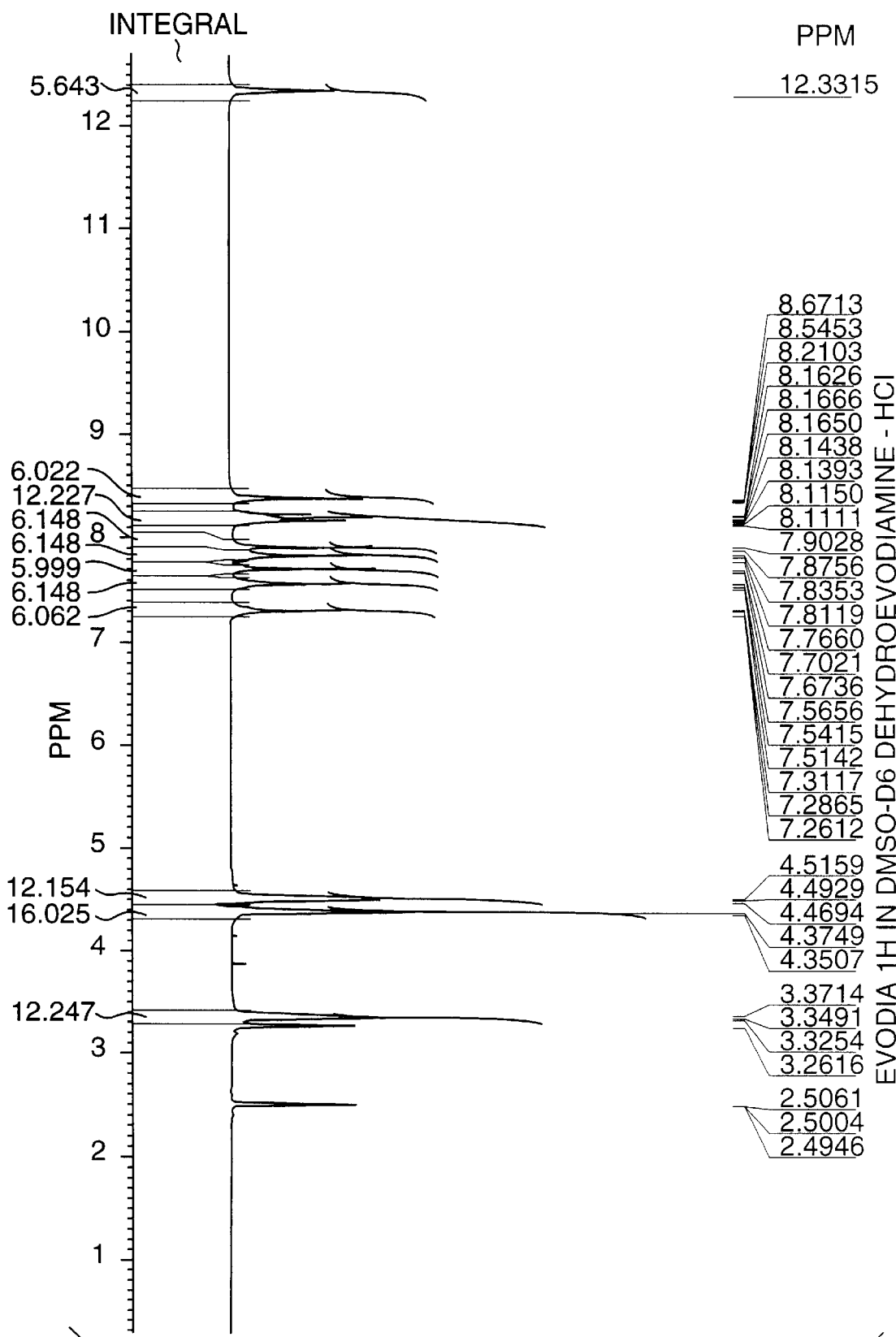
FIG. 2. Nuclear magnetic resonance (NMR) on DHED.
Figure 3:
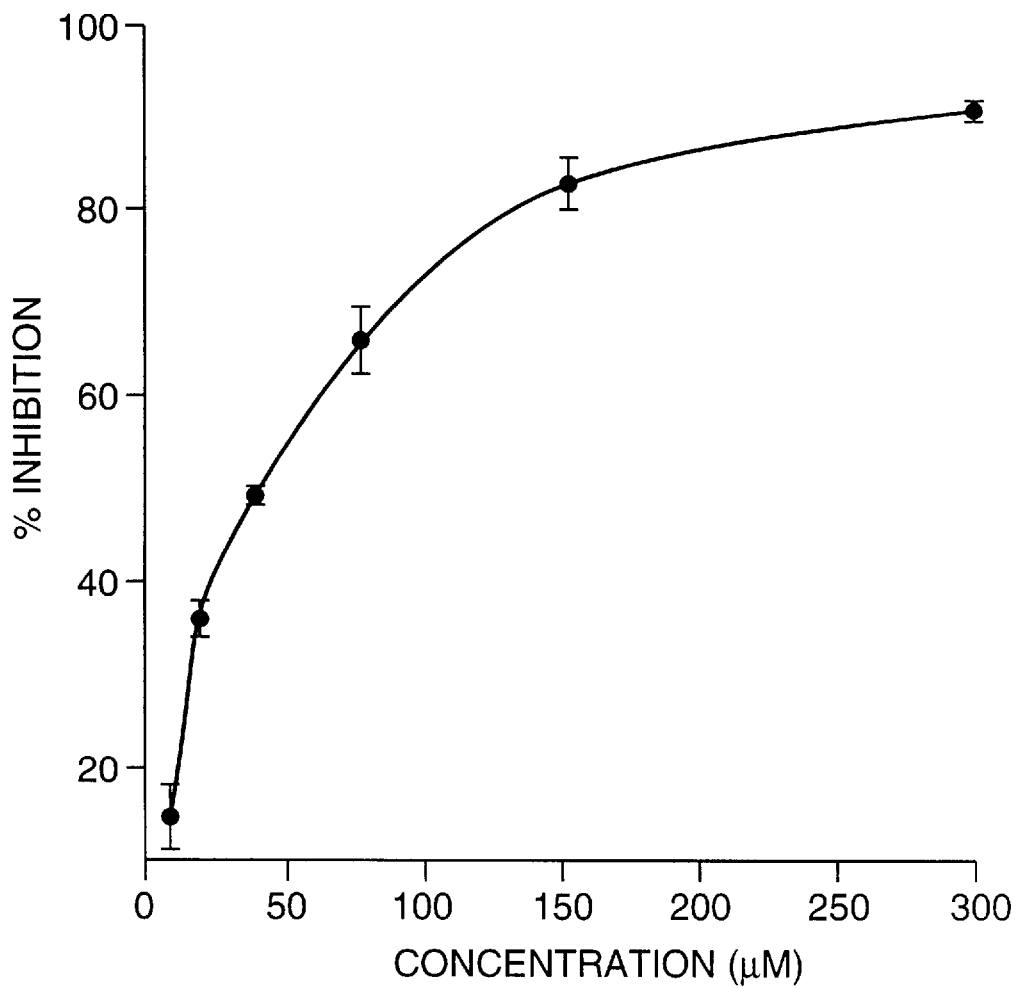
FIG. 3. Dose-dependent inhibition of acetylcholinesterase activity by dehydroevodiamine hydrochloride. Each value represents mean±S. E. (n=5). The inhibition efficacy was expressed as a percentage of enzyme activity inhibited compared with the control value (100%).
Figure 4:
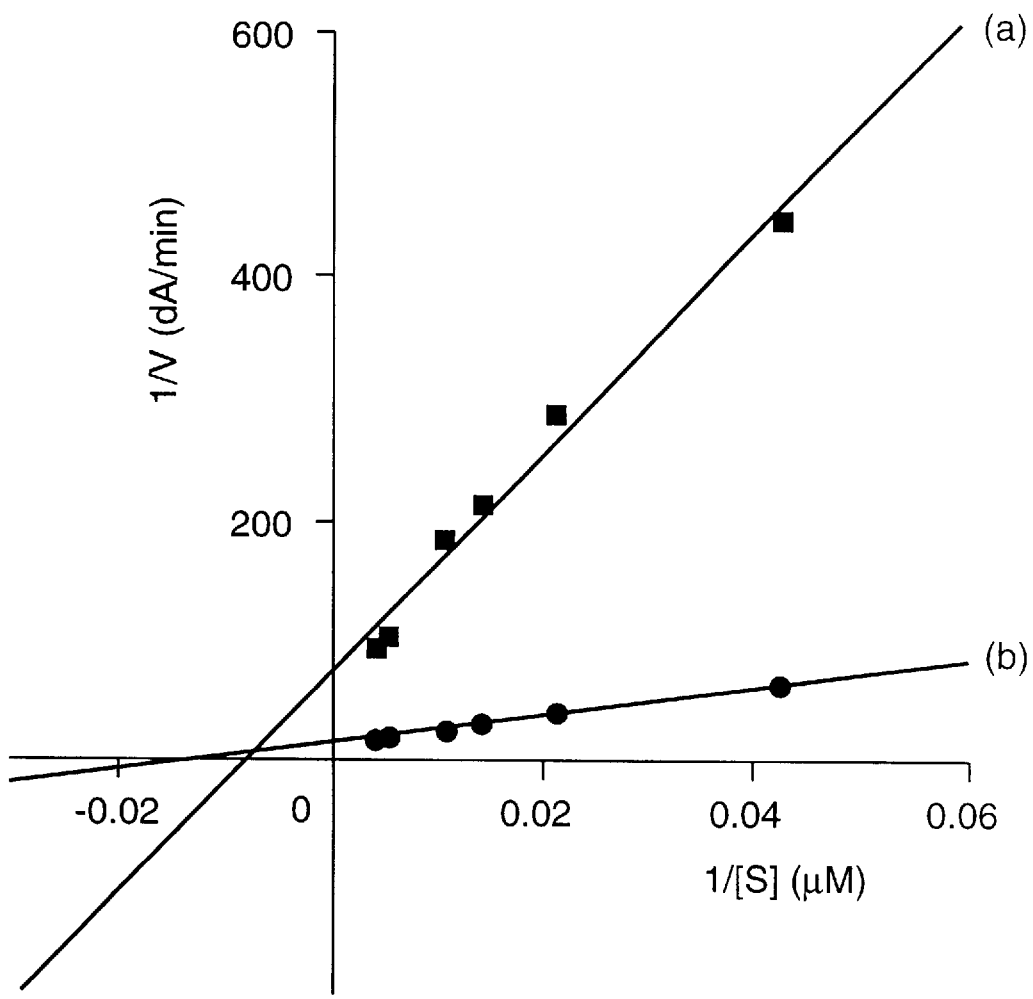
FIG. 4. Lineweaver-Burk plots of AChE activity over a range of substrate concentrations (23 to 230 $\mu$M) in the presence (a) (filled square) or absence (b) (filled circle) of DHED (40 $\mu$M).
Figure 5:
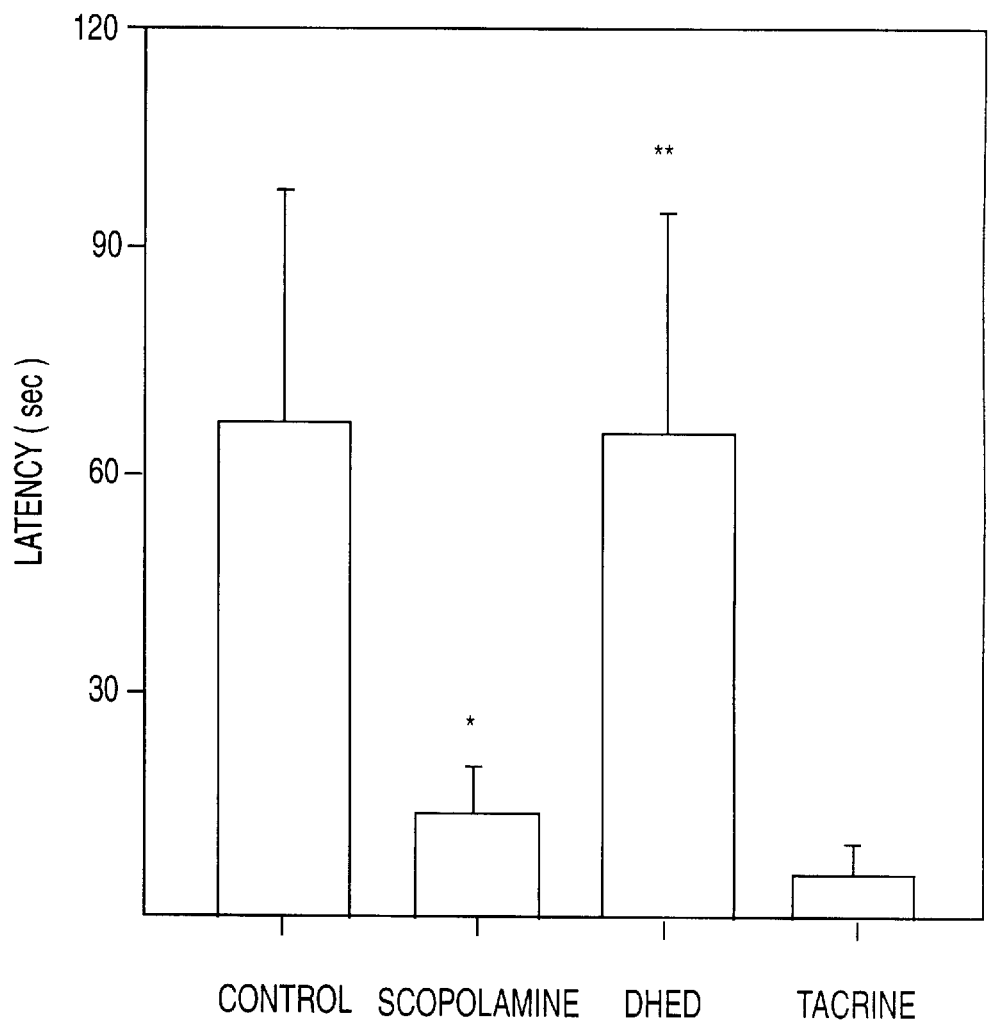
FIG. 5. Effect of a single administration of DHED or tacrine on the memory deficits produced by scopolamine in the passive avoidance test. DHED or tacrine (6.25 mg/kg) was pretreated to rats at 30 min before the injection of scopolamine (1 mg/kg). Data represents mean±S. E. (n=5). * represents significantly different from the saline control group (p<0.05 by Wilcoxon rank sum test). ** represents significantly different from the scopolamine treated group (p<0.05 by Wilcoxon rank sum test).
Figure 6:
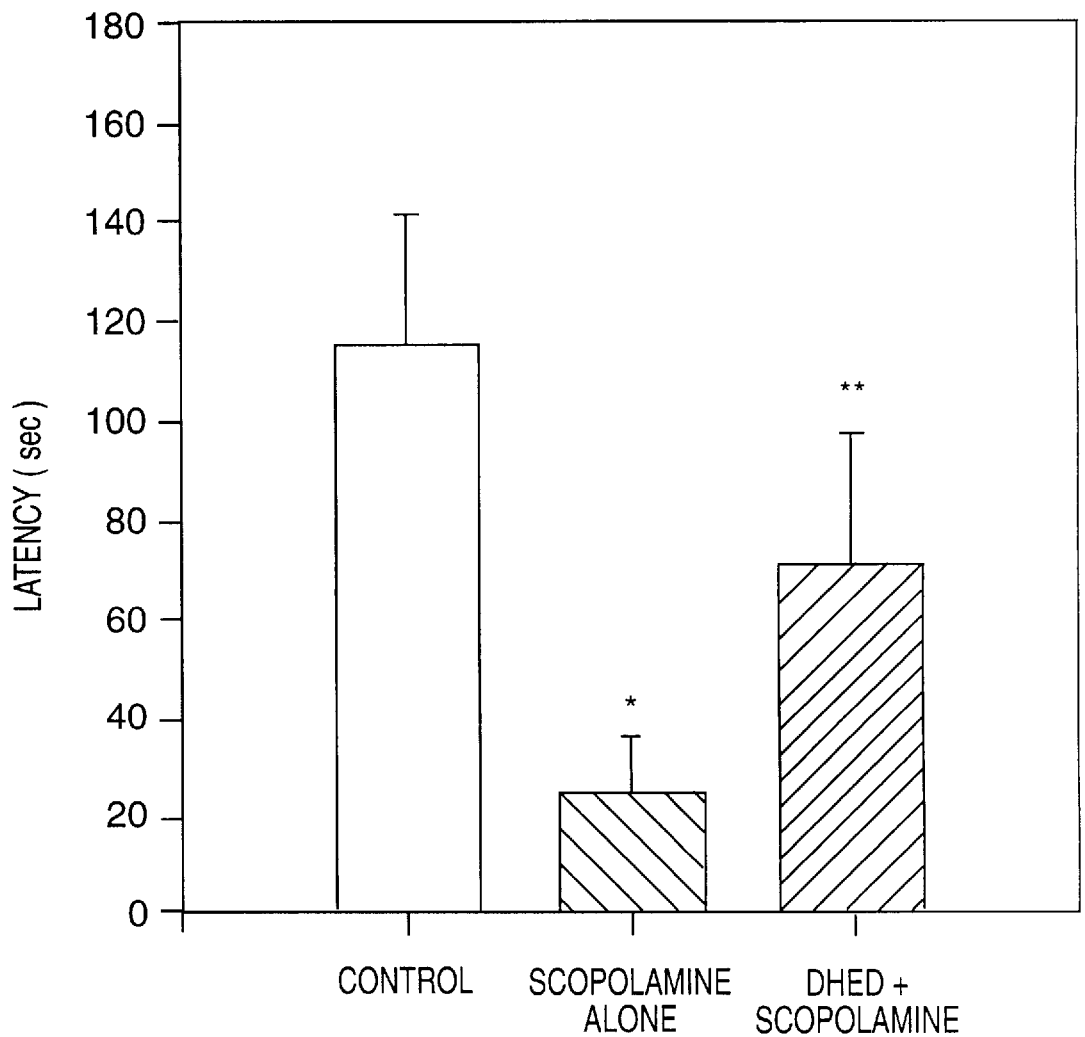
FIG. 6. Effects of repeated administration (once daily for 5 days) of DHED on the memory deficits produced by scopolamine (1 mg/kg). Each value represents mean±S. E. (n=10). * represents significantly different from the saline control group (p<0.05 by Wilcoxon-rank sum test). ** represents significantly different from the scopolamine control group (p<0.05 by Wilcoxon-rank sum test).

What is claimed is:

1. A method for treating dementia in a patient, comprising:
    administering an effective amount of an anti-dementia agent to the patient, wherein the anti-dementia agent includes a pharmaceutically acceptable carrier and dehydroevodiamine-HCl expressed by formula (I) as an active ingredient, wherein formula (I) is as follows:

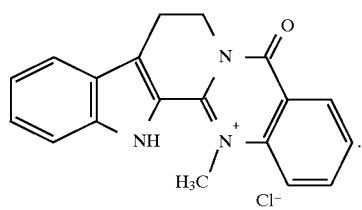

2. A method according to claim 1, wherein the dementia is senile dementia.

3. A method according to claim 1, wherein the dementia is vascular dementia.

4. A method according to claim 1, wherein the anti-dementia agent is administered intravenously.

5. A method according to claim 1, wherein the anti-dementia agent is administered orally.

6. A method according to claim 1, wherein the anti-dementia agent is administered subcutaneously.

7. A method according to claim 1, wherein the anti-dementia agent is administered intramuscularly.

8. A method according to claim 1, wherein the anti-dementia agent is administered by injection.

9. A method for inhibiting acetylcholinesterase activity, comprising:
    administering an effective amount of a pharmaceutical composition to a patient to inhibit acetylcholinesterase activity, wherein the pharmaceutical composition includes a pharmaceutically acceptable carrier and dehydroevodiamine-HCl expressed by formula (I) as an active ingredient, wherein formula (I) is as follows:

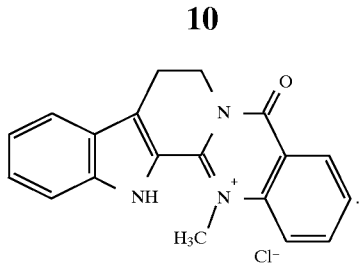

10. A method according to claim 9, wherein the pharmaceutical composition is administered orally.

11. A method according to claim 9, wherein the pharmaceutical composition is administered subcutaneously.

12. A method according to claim 9, wherein the pharmaceutical composition is administered intramuscularly.

13. A method according to claim 9, wherein the pharmaceutical composition is administered by injection.

14. A method for treating amnesia in a patient, comprising:
    administering an effective amount of a pharmaceutical composition to the patient, wherein the pharmaceutical composition includes a pharmaceutically acceptable carrier and dehydroevodiamine-HCl expressed by formula (I) as an active ingredient, wherein formula (I) is as follows:

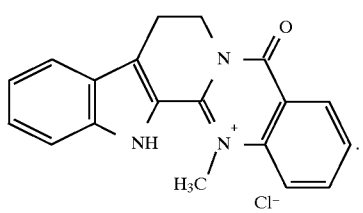

15. A method according to claim 14, wherein the pharmaceutical composition is administered orally.

16. A method according to claim 14, wherein the pharmaceutical composition is administered subcutaneously.

17. A method according to claim 14, wherein the pharmaceutical composition is administered intramuscularly.

18. A method according to claim 14, wherein the pharmaceutical composition is administered by injection.

19. A method for enhancing memory in a patient, comprising:
    administering an elective amount of a pharmaceutical composition to the patient to enhance the memory, wherein the pharmaceutical composition includes a pharmaceutically acceptable carrier and dehydroevodiamine-HCl expressed by formula (I) as an active ingredient, wherein formula (I) is as follows:

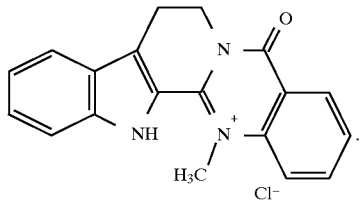

20. A method according to claim 19, wherein the pharmaceutical composition is administered orally.

21. A method according to claim 19, wherein the pharmaceutical composition is administered subcutaneously.

22. A method according to claim 19, wherein the pharmaceutical composition is administered intramuscularly.

23. A method according to claim 19, wherein the pharmaceutical composition is administered by injection.

* * * * *

UNITED STATES PATENT AND TRADEMARK OFFICE
CERTIFICATE OF CORRECTION

PATENT NO. : 5,859,016
DATED : January 12, 1999
INVENTOR(S) : Suh et al.

It is certified that error appears in the above-identified patent and that said Letters Patent is hereby corrected as shown below:

On the Title Page, Item (54), and Col. 1, "HC1" should read --HCL--.

On the Title Page, Item (57), in the Abstract, line 2, after "Benth.", insert a comma --,--.

In Claim 19, col. 10, line 44, "elective" should read --effective--.

Signed and Sealed this

Twentieth Day of July, 1999

*Attest:*

Q. TODD DICKINSON

*Attesting Officer*  Acting Commissioner of Patents and Trademarks